United States Patent
Bonutti et al.

(10) Patent No.: US 12,383,735 B2
(45) Date of Patent: Aug. 12, 2025

(54) SYSTEM AND METHOD FOR AFFECTING POROSITY OF TISSUE BARRIERS, INCLUDING BLOOD BRAIN BARRIER

(71) Applicant: Realeve, LLC, Manalapan, FL (US)

(72) Inventors: Peter M. Bonutti, Manalapan, FL (US); Justin E. Beyers, Effingham, IL (US); Tonya M. Bierman, Dieterich, IL (US)

(73) Assignee: P TECH, LLC, Manalapan, FL (US)

( * ) Notice: Subject to any disclaimer, the term of this patent is extended or adjusted under 35 U.S.C. 154(b) by 0 days.

(21) Appl. No.: 18/649,710

(22) Filed: Apr. 29, 2024

(65) Prior Publication Data

US 2024/0359005 A1    Oct. 31, 2024

Related U.S. Application Data

(60) Provisional application No. 63/550,396, filed on Feb. 6, 2024, provisional application No. 63/549,908, filed (Continued)

(51) Int. Cl.
*A61N 1/32* (2006.01)
*A61N 1/05* (2006.01)

(52) U.S. Cl.
CPC .......... *A61N 1/327* (2013.01); *A61N 1/0526* (2013.01)

(58) Field of Classification Search
CPC . A61N 1/327; A61N 1/36082; A61N 1/36103
See application file for complete search history.

(56) References Cited

U.S. PATENT DOCUMENTS

| 6,405,079 B1 | 6/2002 | Ansarinia |
| 6,429,217 B1 | 8/2002 | Puskas |

(Continued)

FOREIGN PATENT DOCUMENTS

| CN | 113368386 A | 9/2021 |
| WO | 2004010923 A2 | 2/2004 |
| WO | 2025106975 A1 | 5/2025 |

OTHER PUBLICATIONS

Schmidt et al., "Sphenopalatine ganglion stimulation is a reversible and frequency dependent modulator of the blood-brain barrier", Brain Research (Year: 2019).*

(Continued)

*Primary Examiner* — George R Evanisko
(74) *Attorney, Agent, or Firm* — Stinson LLP

(57) ABSTRACT

An electrical stimulation device for modulating a blood-brain barrier (BBB) of a subject includes at least one electrode configured to delivery electrical stimulation to the subject to stimulate a sphenopalatine ganglion (SPG) of the subject, and a control unit in communication with the at least one electrode. The control unit generates a first electrical stimulation signal to the at least one electrode to apply a first electrical stimulation to the subject to stimulate a sphenopalatine ganglion (SPG) of the subject thereby increasing porosity of the BBB from an initial porosity to an increased porosity, and generate, after said first electrical stimulation signal, a second electrical stimulation signal to the at least one electrode to apply a second electrical stimulation to the subject to stimulate the SPG of the subject thereby decreasing porosity of the BBB from the increased porosity to a decreased porosity that is less than the increased porosity.

11 Claims, 11 Drawing Sheets

Related U.S. Application Data on Feb. 5, 2024, provisional application No. 63/578,824, filed on Aug. 25, 2023, provisional application No. 63/498,941, filed on Apr. 28, 2023.

(56) References Cited

U.S. PATENT DOCUMENTS

| | | |
|---|---|---|
| 6,432,986 B2 | 8/2002 | Levin |
| 6,479,523 B1 | 11/2002 | Puskas |
| 6,491,940 B1 | 12/2002 | Levin |
| 6,526,318 B1 | 2/2003 | Ansarinia |
| 6,656,960 B2 | 12/2003 | Puskas |
| 6,778,854 B2 | 8/2004 | Puskas |
| 6,885,888 B2 | 4/2005 | Rezai |
| 7,117,033 B2 | 10/2006 | Shalev et al. |
| 7,142,910 B2 | 11/2006 | Puskas |
| 7,310,552 B2 | 12/2007 | Puskas |
| 7,340,299 B2 | 3/2008 | Puskas |
| 7,477,945 B2 | 1/2009 | Rezai et al. |
| 7,532,938 B2 | 5/2009 | Machado et al. |
| 7,561,919 B2 | 7/2009 | Shalev et al. |
| 7,636,597 B2 | 12/2009 | Gross et al. |
| 7,657,316 B2 | 2/2010 | Jaax et al. |
| 7,684,859 B2 | 3/2010 | Shalev et al. |
| 7,799,337 B2 | 9/2010 | Levin |
| 7,860,569 B2 | 12/2010 | Solberg et al. |
| 8,010,189 B2 | 8/2011 | Shalev |
| 8,055,347 B2 * | 11/2011 | Lamensdorf ....... A61N 1/36082 607/45 |
| 8,206,369 B2 | 6/2012 | Ansarinia |
| 8,229,571 B2 | 7/2012 | Lorian et al. |
| 8,283,793 B2 | 10/2012 | Pless |
| 8,311,632 B2 | 11/2012 | Pless et al. |
| 8,339,262 B2 | 12/2012 | Pless |
| 8,355,779 B2 | 1/2013 | Ansarinia |
| 8,394,075 B2 | 3/2013 | Ansarinia |
| 8,406,869 B2 | 3/2013 | Lamensdorf et al. |
| 8,412,336 B2 | 4/2013 | Pless et al. |
| 8,473,062 B2 | 6/2013 | Pless |
| 8,494,641 B2 | 7/2013 | Boling et al. |
| 8,686,858 B2 | 4/2014 | Pless |
| 8,781,574 B2 | 7/2014 | Pless et al. |
| 8,870,773 B2 | 10/2014 | Narouze |
| 8,954,149 B2 | 2/2015 | Shalev |
| 8,958,881 B2 | 2/2015 | Lamensdorf et al. |
| 8,983,609 B2 | 3/2015 | Rezai et al. |
| 9,211,133 B2 | 12/2015 | Papay |
| 9,220,524 B2 | 12/2015 | Boling et al. |
| 9,233,245 B2 | 1/2016 | Lamensdorf et al. |
| 9,320,908 B2 | 4/2016 | Fletcher et al. |
| 9,456,836 B2 | 10/2016 | Boling et al. |
| 9,550,057 B2 | 1/2017 | Papay et al. |
| RE46,307 E | 2/2017 | Ansarinia |
| RE46,332 E | 3/2017 | Ansarinia |
| 9,604,057 B2 | 3/2017 | Caparso |
| 9,607,195 B2 | 3/2017 | Pless |
| 9,610,441 B2 | 4/2017 | Goodman et al. |
| 9,662,140 B2 | 5/2017 | Powell et al. |
| 9,700,721 B2 | 7/2017 | Goodman et al. |
| 9,757,572 B2 | 9/2017 | Boling et al. |
| 9,763,581 B2 | 9/2017 | Bonutti et al. |
| 9,861,295 B2 | 1/2018 | Powell et al. |
| 10,058,393 B2 | 8/2018 | Bonutti et al. |
| 10,068,318 B2 | 9/2018 | Dzyubak et al. |
| 10,098,662 B2 | 10/2018 | Boling et al. |
| 10,286,213 B2 | 5/2019 | Fletcher et al. |
| 10,322,279 B2 | 6/2019 | Papay |
| 11,478,641 B2 | 10/2022 | Luhrs et al. |
| 11,679,263 B2 | 6/2023 | Hsu et al. |
| 11,687,800 B2 | 6/2023 | Bonutti et al. |
| 11,883,665 B2 | 1/2024 | Hsu et al. |
| 2002/0008723 A1 | 1/2002 | Hsu et al. |
| 2005/0074506 A1 | 4/2005 | Natan et al. |
| 2005/0266099 A1 | 12/2005 | Shalev |
| 2006/0020299 A1 | 1/2006 | Shalev |
| 2009/0210026 A1 | 8/2009 | Solberg et al. |
| 2009/0299418 A1 | 12/2009 | Shalev et al. |
| 2012/0253261 A1 | 10/2012 | Poletto et al. |
| 2013/0184803 A1 | 7/2013 | Altman |
| 2016/0151646 A1 | 6/2016 | Bonutti et al. |
| 2021/0178154 A1 | 6/2021 | Bonutti et al. |
| 2021/0401507 A1 | 12/2021 | Stylos et al. |
| 2022/0101999 A1 | 3/2022 | Bonutti et al. |

OTHER PUBLICATIONS

Mordor Intelligence, Neurodegenerative Disease Market Size & Share Analysis—Growth Trends & Forecasts (2024-2029) 7 pages, Jan. 29, 2024, https://www.mordorintelligence.com/industry-reports/neurodegenerative-disease-market.

Thiel et al., Forumm Mini-Review, Nitric Oxide and Blood-Brain Barrier Integrity, Antioxidants & Redox Signaling, vol. 3, No. 2, pp. 273-278, (2001), Mary Ann Liebert, Inc.

Alahmari, A., Blood-Brain Barrier Overview: Structural and Functional Correlation, Hindawi Neural Plasticity vol. 2021, Article ID 6564585, Dec. 6, 2021, 10 pages, https://doi.org/10.1155/2021/6564585.

Biose et al., Promising Cerebral Blood Flow Enhancers in Acute Ischemic Stroke, Transl. Stroke Res., vol. 14, pp. 863-889, (2023) Nov. 17, 2022, https://doi.org/10.1007/s12975-022-01100-w.

Bornstein, MD, et al., Sphenopalatine Ganglion Stimulation to Augment Cerebral Blood Flow a Randomized, Sham-Controlled Trail vol. 50, No. 8, May 23, 2019, 17 pages, Stroke https://doi.org/10.1161/STROKEAHA.118.024582.

European Extended Search Report for Application No. 241731900, Sep. 16, 2024, 8 pages, Germany.

Hosseini et al, Mechanisms of action of acute and subacute sphenopalatine ganglion stimulation for ischemic stroke, International Journal of Stroke, Apr. 23, 2020, vol. 15(8) 839848, https://journals.sagepub.com/doi/10.1177/1747493020920739.

Khurana et al. Implant for Augmentation of Cerebral Blood Flow Trial-1 (ImpACT-1). A single-arm feasibility study evaluating the safety and potential benefit of the Ischemic Stroke System for treatment of acute ischemic stroke, Jul. 3, 2019, 14 pages, https://doi.org/10.1371/journal.pone.0217472.

Lang, MD et al., 155 Enhanced Stem Cell Delivery by Functional Blood-Brain Barrier Modulation Improves Neurological Recovery in a Rodent Stroke Model, Neurosurgery, vol. 63, pp. 162-163, Aug. 2016, https://doi.org/10.1227/01.neu.0000489724.69358.b7.

Levi et al., Stimulation of the Sphenopalatine Ganglion Induces Reperfusion and Blood-Brain Barrier Protection in the Photothrombotic Stroke, Jun. 22, 2012, 10 pages, https://doi.org/10.1371/journal.pone.0039636.

Puris, E. et al., Targeting Transporter for Drug Delivery to the Brain: Can we do Better?, Mar. 31, 2022, 41 pages, Pharmaceutical Research (2002) 39:1415-1455.

Saver, MD, et al., Refined Sphenopalatine Ganglion Stimulator Placement and Intensity Setting to Augment Blood Flow and Neurologic Function, Stroke, vol. 50, No. 12, Nov. 19, 2019, https://doi.org/10.1161/STROKEAHA.119.027177.

Schmidt et al., Sphenopalatine Ganglion Stimulation is a Reversible and Frequency-Dependent Modulator of the Blood-Brain Barrier, Apr. 26, 2019, Brain Research 1718, pp. 231-241, https://doi.org/10.1016/j.brainres.2019.04.030.

Stricsek MD et al., 221 Functional Modulation of the Blood Brain Barrier, Neurosurgery, vol. 64, Issue CN suppl. 1, p. 260, Sep. 1, 2017, https://doi.org/10.1093/neuros/nyx417.221.

Stamatovic et al., Junctional proteins of the blood-brain barrier: New insights into function and dysfunction, Jan., Feb., Mar. 2016, 12 pages, Taylor.

Stroke Management Market Poised to Surge from $36.94 Billion to $39.00 Billion in 2024, Jan. 28, 2028, https://finance.yahoo.com/news/stroke-management-market-poised-surge-005600586.html, Research and Markets, Dublin.

Tamayo et al., Regulation of Blood Flow in the Cerebral Posterior Circulation by Parasympathetic Nerve Fibers: Physiological Background and Possible Clinical Implications in Patients with

(56) References Cited

OTHER PUBLICATIONS

Vertebrobasilar Stroke, Front. Neurol., Stroke, vol. 12, Oct. 29, 2021, https://doi.org/10.3389/fneur.2021.660373.

Tepper et al., Acute Treatment of Intractable Migraine with Sphenopalatine Ganglion Electrical Stimulation, Jul. 6, 2009, American Headache Society, https://doi.org/10.1111/j.1526-4610.2009.01451.x.

Theofanis, MD, et al. Sphenopalatine Ganglion Stimulation Upregulates Transport of Intra-Arterial Temozolomide Across the Blood-Brain Barrier, Neurosurgery, 66(Supplement_1):p. 310-151, Sep. 2019, https://doi.org/10.1093/neuros/nyz310_151.

Yarnitsky, et al., Bloodbrain barrier opened by stimulation of the parasympathetic sphenopalatine ganglion: a new method for macromolecule delivery to the brain, J Neurosurg. 101:303309, Aug. 2004.

Schoenen et al, Stimulation of the Sphenopalatine ganglion (SPG) for cluster headache treatment. Pathway CH 1: a randomized sham—controlled study, Cephalalia an International Journal of Headache, vol. 33, Issue 10, pp. 816-830, Jul. 10, 2013, https://doi.org/10.1177/0333102412473667.

Goadsby MD, P., et al., Safety and Efficacy of sphenopalatine ganglion stimulation for chronic cluster headache: a double-blind, randomized controlled trial, Lancet Neurology, Dec. 2019, pp. 1081-1090, vol. 18—Issue 12, Elsevier Ltd.

Feigin et al., World Stroke Organization (WSO): Global Stroke Fact Sheet 2022, International Journal of Stroke, Jan. 5, 2022, pp. 18-29, vol. 17—Issue 1, World Stroke Organization.

Yarnitsky et al., Increased BBB permeability by parasympathetic sphenopalatine ganglion stimulation in dogs, Brain Research, Aug. 27, 2004, pp. 236-240, vol. 1018—Issue 2, Elsevier B.V. (Abstract and Introduction; not full article).

Preview Article found at https://www.sciencedirect.com/science/article/abs/pii/S1094715921069671#preview-section- snippets, for POWELL et al., The Potential Role of Neuromodulation in Subarachnoid Hemorrhage, Neuromodulation: Technology at the Neural Interface, Dec. 2, 2022, pp. 1215-1226, vol. 25-Issue 8, Elsevier Inc.

\* cited by examiner

W = pulse width
D = inter phase interval
T = inter pulse interval

Amplitude Modulated Biphasic Waveform

Frequency modulated pulse width

Frequency modulated inter pulse interval

:Stand Alone Operation

:Tethered Operation

:Wireless Operation
(Passthrough)

:IOT Operation

SYSTEM AND METHOD FOR AFFECTING POROSITY OF TISSUE BARRIERS, INCLUDING BLOOD BRAIN BARRIER

CROSS-REFERENCE TO RELATED APPLICATIONS

The present application claims the benefit of priority to U.S. Provisional Application Ser. No. 63/498,941, filed Apr. 28, 2023; 63/578,824, filed Aug. 25, 2023; 63/549,908, filed Feb. 5, 2024; and 63/550,396, filed Feb. 6, 2024. The entirety of each of these applications is incorporated by reference herein.

FIELD OF THE DISCLOSURE

The present disclosure generally relates to a method and system for using stimulation (e.g., electrical stimulation) to open and/or close a tissue barrier (e.g., the blood-brain barrier) to enable delivery of a drug (i.e., an active agent) to a patient's tissue (e.g., brain tissue) and/or drainage or removal of biologicals (e.g., blood) and/or waste.

BACKGROUND OF THE DISCLOSURE

The body includes tissue barriers, such as blood vessels, membranes, other tissues, to limit transport of particles across the barrier to other tissues. For example, the blood-brain barrier (BBB) is a highly specialized and selectively permeable membrane that separates the circulating blood from the brain tissue. It is formed by a layer of tightly packed endothelial cells that line the capillaries in the brain. These endothelial cells are bound together by tight junctions and surrounded by pericytes, astrocytes, and basement membrane, which provide structural support to the BBB.

The BBB plays a crucial role in maintaining a stable environment for the brain by regulating the passage of substances between the bloodstream and the brain tissue. It allows the passage of essential nutrients such as glucose and oxygen while restricting the entry of harmful substances such as toxins and pathogens. This selective permeability is achieved through several mechanisms, including active transport, receptor-mediated transport, and enzymatic degradation.

The BBB also helps to protect the brain from fluctuations in the levels of hormones, neurotransmitters, and other chemicals in the bloodstream. It also prevents the entry of large molecules such as proteins and immune cells, which can trigger inflammation and damage the brain tissue.

However, the BBB can also pose a challenge in the treatment of neurological disorders, as it can limit the delivery of drugs to the brain. Researchers are exploring various strategies to overcome this barrier, such as using nanoparticles or modifying the properties of the drugs to enable them to cross the BBB.

DETAILED DESCRIPTION OF THE DISCLOSURE

Figure 1:
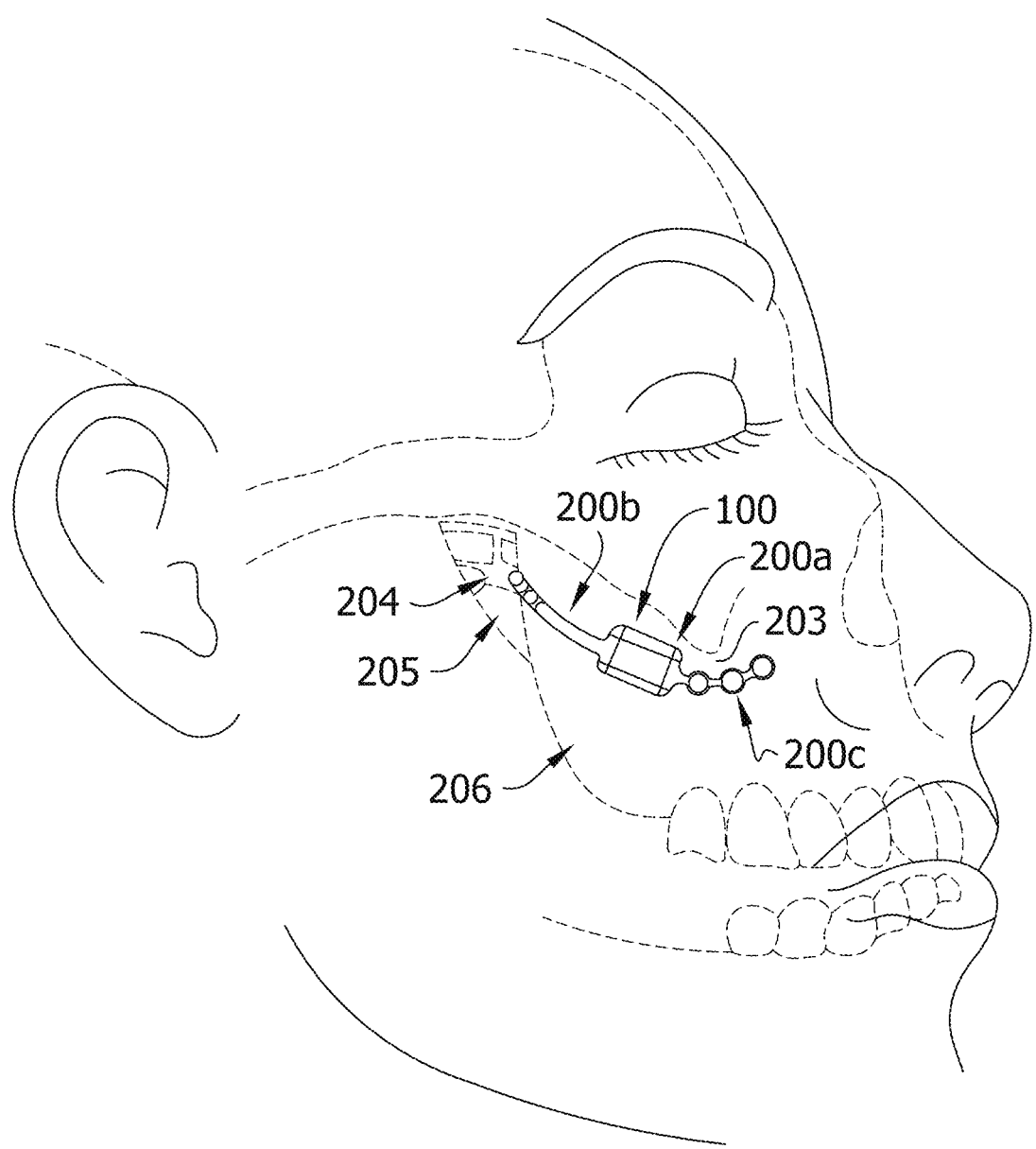
FIG. 1 is a schematic representation of one embodiment of a stimulator implanted extra-cranially in a human body.

In one embodiment, a method of delivering one or more active agents (e.g., medicine, drugs, other agents) through the blood-brain barrier (BBB) and into brain tissue is described. Stimulation, such as electrical stimulation, ultrasound, or other stimulation or energy, is used to affect porosity of the BBB (e.g., increase porosity of larger molecules or types of molecules) to enable the active agent to cross into brain tissue. In other embodiments, a system and method includes stimulation used to affect porosity (i.e., increase porosity) of other barriers of the body (e.g., bursac wall, synovial membrane, blood vessels, etc.) and delivery of one or more active agents through the barrier after stimulation and into tissue or space enclosed or surrounded by the barrier. The systems and methods described herein may be configured to increase porosity of the barrier during a first step to enable delivery of the active agent through the barrier, and then during a subsequent second step after a predetermined or other parameter, decrease the porosity of the barrier to inhibit other molecules and/or additional amounts of active agent from passing through the barrier. Broadly, the systems and methods may "open" the barrier and then subsequently "close" the barrier upon a determining a predetermined parameter, such as time or active agent concentration in the tissue. As used herein, to "open" the barrier (and other "open" iterations) means increasing the overall porosity and/or the selective porosity of types or sizes of molecules to enable selective molecule parameters to pass through the barrier; and to "close" the barrier (and other "close" iterations) means decreasing the overall porosity and/or the selective porosity of types or sizes of molecules to inhibit selective molecule parameters from passing through the barrier.

In another embodiment, systems and methods described herein may be used to open the barrier (and optional close) without the use of one or more active agents to increase function of the barrier. For example, systems and methods may be used to facilitate stroke rehabilitation. In another embodiment, the stimulator implant can be used arterially or percutaneously. The lead or electrode portion of the implant can also be designed such that components or the entire system is biodegradable.

In yet another embodiment, systems and methods described herein may be used to open (and then close) the BBB to enable larger molecules to exit the brain for diagnostic purposes. For example, the BBB may be opened, such as using a method described herein, whereby larger molecules that are typically tested for using a spinal tap may enter the blood stream and can be detected by withdrawing blood from blood stream rather than the spinal tap. Opening (and subsequent closing) of the BBB or other membrane may also be used for drainage purposes.

In one exemplary method, the active agent may be delivered adjacent or to the BBB via a catheter or other means. The suitable stimulation is applied (before, after or simultaneously with delivery of the active agent) to increase and/or later the porosity of the BBB to enable the active agent to pass through the BBB into brain tissue. In one example, an indwelling catheter or other delivery device can controllably release the active agent. This device may be controlled by a controller (microprocessor and memory) and operated in conjunction with an indwelling stimulation device suitable to deliver stimulation for affecting the BBB to enable delivery of the active agent into brain tissue. Such agent-delivery and stimulation devices are described in more detail below. The method may be used with oxygen therapy (such as, hyperbaric oxygen therapy—in a chamber) or used as adjunct to chamber or medication, or thermal therapy to open BBB or to relieve vasospasm or transcutaneous delivery of medication or treatment.

In one or more examples, which may be applied to any other example described herein, the active agent for passing through the BBB may include, but is not limited to, one or more of: drugs for Alzheimer's, chemotherapy agents, amyloid deposit removal agents, agents to enhance biologic byproduct reduction, stimulants or depressors, proteins, enzymes, hormones, other agents to enhance drainage of toxic or harmful compounds. Among other functions, active agent(s) may be used for stroke, cancer, Alzheimer's, depression, stress, sleep, psychosis, infection, vision, memory, delivery of DNA or RNA fragments with or without virus or other carrier for genetic disease, condition treatment, enhancement of brain function, atypical facial pain, cranial nerve or other pain or disease.

The method described herein can be used for therapy for treating concussion or CTS or other brain injuries or other CNS disorder or relieve or reduce symptoms. It may be used to treat agitation or aggressive or other dysfunctional behavior. If identified early, the method can be used in therapies in utero, which can be used to treat cerebral palsy or neonatal hypoxia, or treat neonate in late term pregnancy for genetic diseases or deficiencies. For example, such therapies would involve delivering enzymes, hormones, DNA or RNA into brain tissue of embryo or fetus. In one example, the biologic agent may be used in conjunction with gene editing tools, such as CRISPR-Cas9 technology, to enable in utero gene editing. Diseases such as osteogenesis imperfect to mutations to Huntingtons or infections such as toxoplasmosis or meningitis can be treated using the methods and systems described herein. The methods and systems can be used to enhance neuroplasticity and help CNS tissue or nerve fibers regrow or heal after anoxia or stroke or chemical, pharmaceutical injury, as non-limiting examples. In one or more embodiments, the method described herein may be used to treat memory loss, cognitive impairment, auto immune disease of CNS, neurodegenerative disorders, ALS, CTE, Parkinson's, and/or vasospasms especially after aneurysms. In one or more embodiments, the method described herein may be used for delivery of one or more of the following across the BBB: monoclonal antibodies, chemotherapy agents, stem cells and biologics, and/or nutrients like lipids, fatty acids, starches, longer chain proteins.

In one example, the stimulation device for affecting the BBB may be designed and constructed to deliver electrical stimulation to the sphenopalatine ganglion (SPG) or other nerve or ganglion, for example. Suitable devices and methods for electrically stimulating the SPG are described in U.S. Ser. No. 17/183,293, filed Feb. 23, 2021; U.S. Ser. No. 17/327,442, filed May 21, 2022; U.S. Ser. No. 12/434,457, filed May 1, 2009; U.S. Ser. No. 13/784,452, filed Mar. 4, 2013; and U.S. Ser. No. 15/362,124, filed Nov. 28, 2016; each of which are incorporated by reference herein in its entirety. FIG. 1 is a reproduced figure of a suitable stimulator disclosed in U.S. Ser. No. 12/434,457. Another suitable device is offered by Brainsgate, for example. Such devices include electrodes for delivering the electrical stimulation. A suitable frequency for stimulation may be below 60 Hz, such as 10 to 30 Hz. The electrodes of the stimulation device can be self-guided or include an ingrowth portion—a roughened or porous or coated surface to remain fixed at a location despite body movement if long term requires or could be partially or completely biodegradable. The stimulation device can include ASICS (which can include a waveform generator, patient safety circuitry, volatile and non-volatile memory, communication modules, sensors and wave form processing circuitry, and cybersecurity functions) or an ingrowth surface or be stabilized with one or more suture anchors or other fasteners couple to tissue or bone for stability.

Other stimulation devices include magnetic stimulation, mechanical stimulation or ultrasound stimulation. Suitable device and methods for ultrasound stimulation is described in U.S. Ser. No. 15/011,156, filed Jan. 29, 2016, the entirety of which is incorporated by reference. In other embodiments, chemical stimulation may be used. For example, acidic or basic fluid, or serotonin, serotonin reuptake inhibitors, or serotonin blockers, or epinephrine or epinephrine blockers, or other chemicals to facilitate stimulation of SPG or otherwise affect BBB porosity (e.g., opening and closing) either at SPG or systemically through an IV or locally with a catheter delivered to the BBB. This chemical stimulation may be used in conjunction with or apart from electrical or other energy-based stimulation.

In one or more examples, the stimulation device may be externally controlled and/or powered, such as by an external control system. One such suitable device is the Pulsante by Realeve company. The control system can alter wavelength, frequency, energy, pulse period, inter pulse period, duty cycle, and/or waveform. The control system may be programmed with one or more functions for controlling the stimulation device. For example, the control system may operate to stimulate for a period of time, then cease operation for a period of time later to enhance control and be multifunctional. As an example, in one aspect the stimulation device may be operated to control pain at one point in time and then at a different point in time used to deliver active agent or relived vasospasm.

The stimulation device may be operated with wearables or remote patient monitoring systems. Encrypted technology that goes through mobile devices wireless or hard wired to cloud may be used to process information to patient provider or insurance company SPG stimulator or external handpiece that controls frequency, power, wavelength etc. can have Bluetooth for data in or out Electronics can be part biodegradable or upgradeable.

The stimulation device may be used with AI systems or other software to add functionality or build up implant to decide optimal function and what to add to implant either internally or to external device. AI can be used to optimize frequency, wavelength, power, and timing with or without other treatment like medical treatment or oxygen or if multiple frequencies or wavelength or power used for an individuals' treatment. Training data for AI software may be gathered from multiple patients' data or a synthetic data set could be created. Additional data may be patient anatomy, biologic functions like food, pulse, oxygen levels, temperature, implant design, electrode design and location and feedback sensor (such as EEG, MEG, MRI, imaging or other invasive and non-invasive sensors) or patients' response notes by wearable or iPhone or video. Teachings described in U.S. Ser. No. 15/299,981, filed Oct. 21, 2016, and U.S. Ser. No. 16/118,025, filed Aug. 30, 2018 (the entirety of each of which is hereby incorporated by reference), are pertinent to these features.

In one or more examples, the agent delivery device (e.g., catheter) can be inserted or implanted and operated using suitable techniques. For example, the agent delivery device may be inserted or implanted using MIS approaches, or an expanding access device, or magnetic or RF guided catheter or guide wire, or a deposition (aerosol) drug delivery system. The agent delivery device can guide or be used with biplanar fluoroscopy or MRI or PET or EM, or with a dye or radiologic marker or technetium 99 or other radioisotope to follow, guide, monitor, direct treatment. One example of a suitable agent delivery device and method is described in U.S. Ser. No. 17/170,710, filed Feb. 8, 2021, the entirety of which is hereby incorporated by reference.

As described in the '710 application, a tissue distraction system may be used with the agent delivery device. The distraction system 260 includes a multi-channel catheter/cannula 262, an expandable balloon 264, a balloon inflation tube 266, and a drug delivery tube 268. In use, the system 260 is inserted in tissue adjacent a body region 272 which requires the administration of one or more medicaments. During insertion, the balloon 264 is deflated to minimize tissue displacement. Once positioned, the balloon 264 is inflated to distract tissue. The distal end of the drug delivery tube 268 is positioned proximal from the balloon 264 such that medicament may be administered to tissue located proximal to the balloon 264.

A distraction drug delivery system 270 is similar to the system 260 and includes similar structural features. In use, the system 270 is inserted in tissue adjacent a body region 272 which requires the administration of one or more medicaments. During insertion, the balloon 264 is deflated to minimize tissue displacement. Once positioned, the balloon 264 is inflated to distract tissue. The distal end of the drug delivery tube 268 is positioned distal from the balloon 264 such that medicament may be administered to tissue located distal to the balloon 264. The systems 260/270 allow therapeutic and pharmaceutical agents to be delivered to a greater tissue surface area since the tissue is spaced apart by the inflated balloon.

A drug dispersion member 280 may be used for administering one or more medicaments to the surface of tissue. The dispersion member 280 includes porous material 284 for allowing medicaments to flow therethrough. The member 280 may be made of foam, fabric, polymer, metal, ceramic, composite, or combinations thereof. It may be biodegradable or biostable. The dispersion member 280 may include a channel 286 dimensioned for receiving a delivery tube 288 of a drug delivery system previously described. The member 280 is implanted in tissue 282 such that the outer surface of the member contacts the tissue surface. The delivery tube 288 is inserted in the channel 286 of the member 280. The tube 288 may include microenvironment-controlling devices, such as sensors 14, magnets 102, heating/cooling units 18, drug ports 16, and pressure ports 16. With the tube positioned, one or more medicaments may be expelled from the tube 288 and captured by the porous material 284 of the disbursement member 280. The member and its pores function as a wick to carry the agent(s) to the adjacent tissue. The microenvironment of the adjacent tissue may be measured, changed, and monitored by the dispersion member.

A remote monitoring system may be used. A suitable patient monitoring system is described in U.S. Pat. No. 9,763,581, the entirety of which is incorporated by reference herein. As described in the '581 patent, one can externally monitor these drug deliveries systems or internally monitor them. The delivery systems could be used with an implantable pump or implantable blood chemistry sensor. A wireless readout from the pump or sensor could attach, for example, to a wrist watch which would monitor the compliance through a digital readout. A patient could monitor their own blood chemistries or response to particular medications and then these results would be broadcast to physician, extended care, nurse practitioner, nurse, insurance carrier, etc. This would then monitor the changes to a specific drug and then monitor the serum chemistries, for example, blood sugar, etc. These are monitored and then the patient can be monitored through a wireless format to see how they respond to certain medications and have an instant readout through this chemistry monitor without actually having the patient in the office or in the hospital. If the response is not as desired, the delivery protocol can be remotely changed based on the measurements.

The system may be used with video documentation systems, as described in U.S. Ser. No. 17/401,898, filed Aug. 13, 2021, the entirety of which is incorporated by reference.

Figure 2:
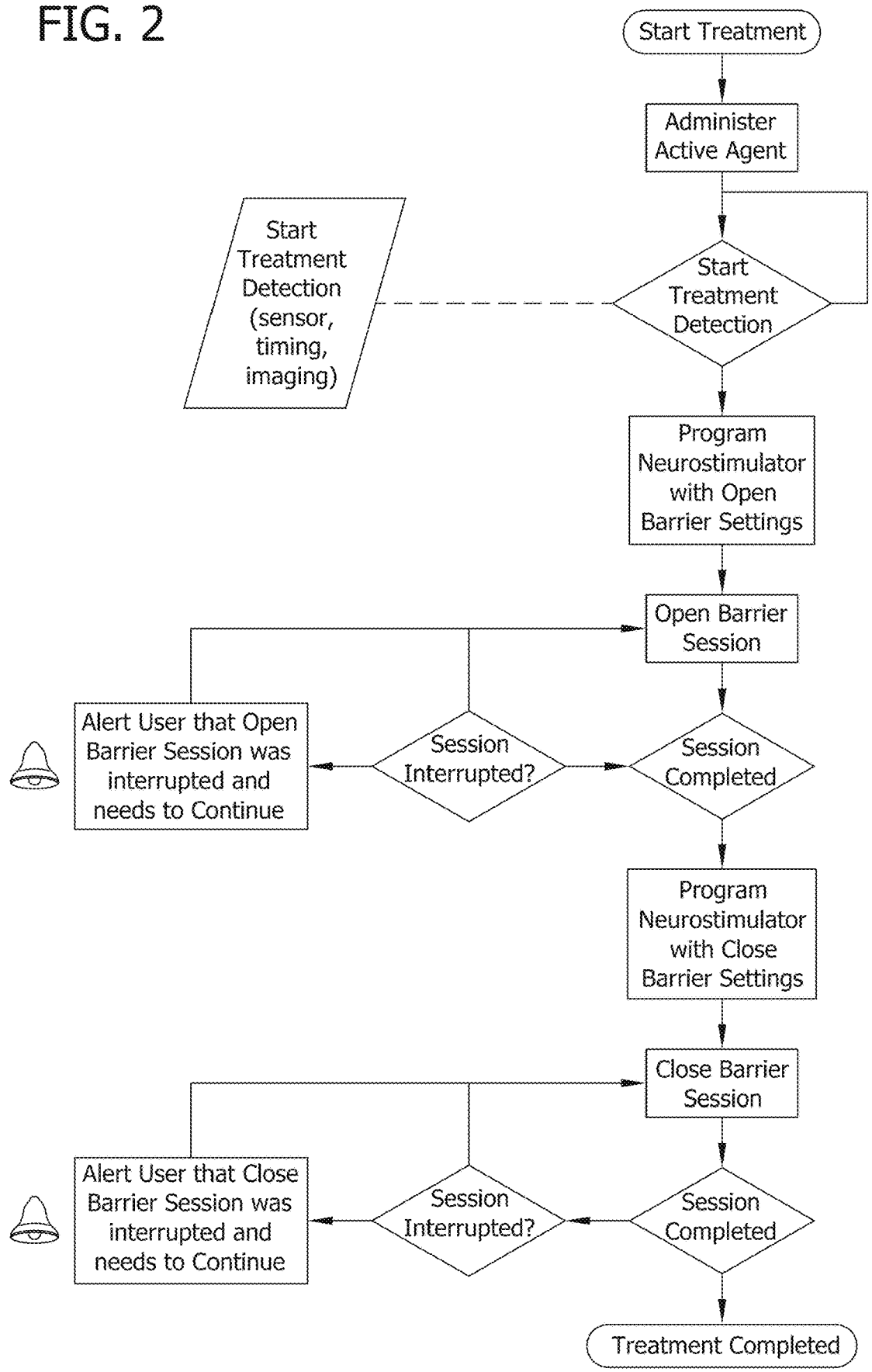
FIG. 2 is a schematic representation of one embodiment of a method of treating tissue by opening and closing a tissue barrier.
Figure 3:
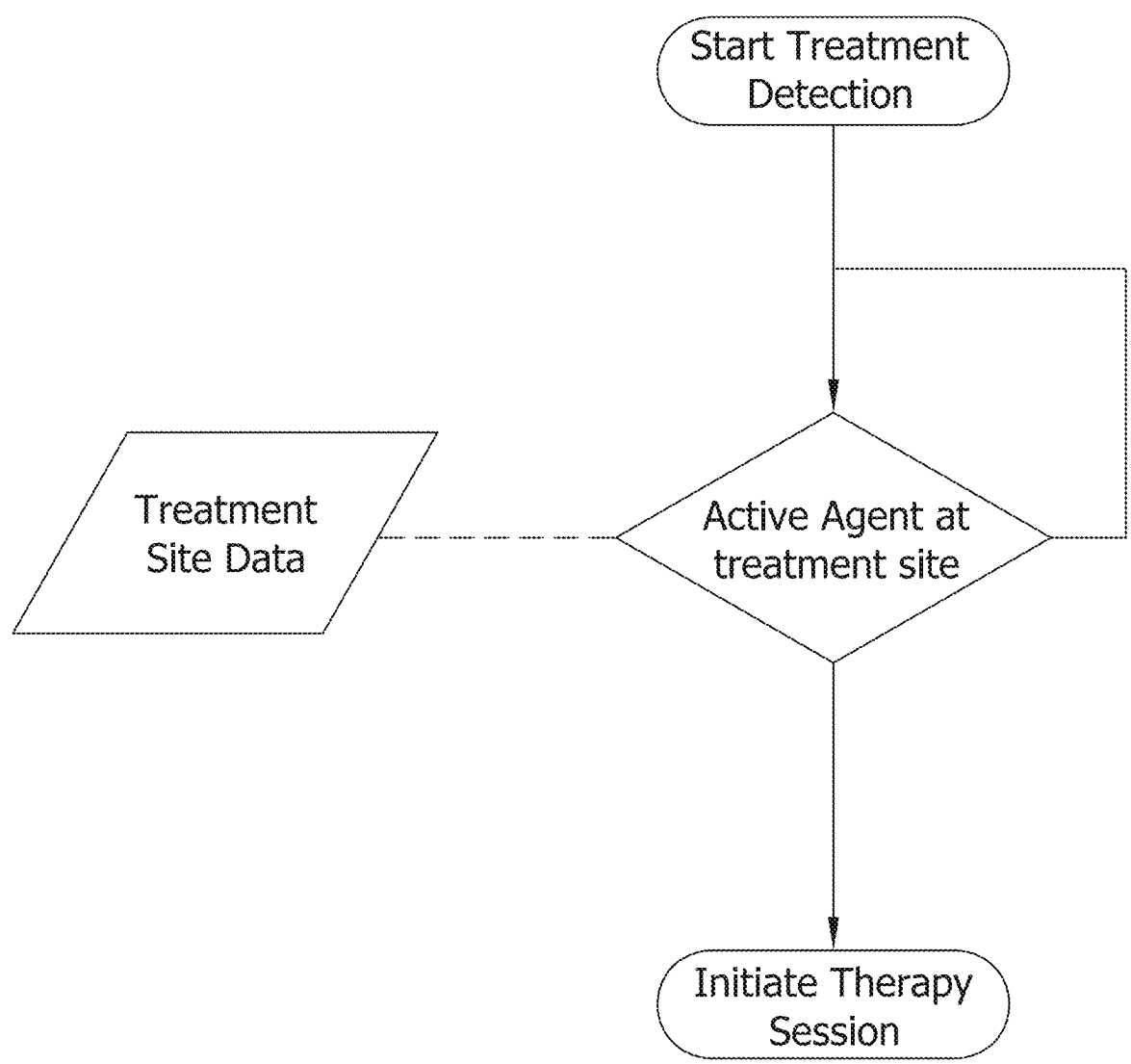
FIG. 3 is a schematic representation of method of detecting when active agents are ready to be passed through the barrier.

An exemplary method of treating a patient by affecting porosity of a barrier of the patient is shown in FIG. 2. An active agent may be administered to the patient (such as by any method described above or other method) before applying the stimulation signal (e.g., electrical signal) to a body portion (e.g., neuron cell bodies—ganglia—such as SPG) to affect porosity of the barrier (e.g., BBB). Referring to FIG. 3, after administrating the agent, a predetermined parameter may be measured and analyzed to determine initiation of stimulation at a subsequent step to "open" the barrier. As non-limiting examples, the predetermined parameter may be time elapsed, delivered active agent dosage, active agent concentration in the body (e.g., around or at the barrier), change in active agent concentration, change of concentration of a substance (e.g., a brain substance) in blood of the subject indicating that the substance has passed through the BBB and into the blood stream, or other parameters. For example, an internal sensor, blood analysis, and/or or imaging may be used to determine concentration of the active agent. In one embodiment, the timing could come directly from integration of an infusion pump to the system. By monitoring the flow rate of the active agent, the delivery time of the therapeutics to the brain can be predicted. As explained below, in one example, a sensor may be integrated with the stimulator or other implant. In another example, a dye or other tag could be used with the active agent and imaging can be used to determine concentration or presence of active agent at the barrier. An imager may be independent or integrated into the system or be independent from the system.

Figure 4:
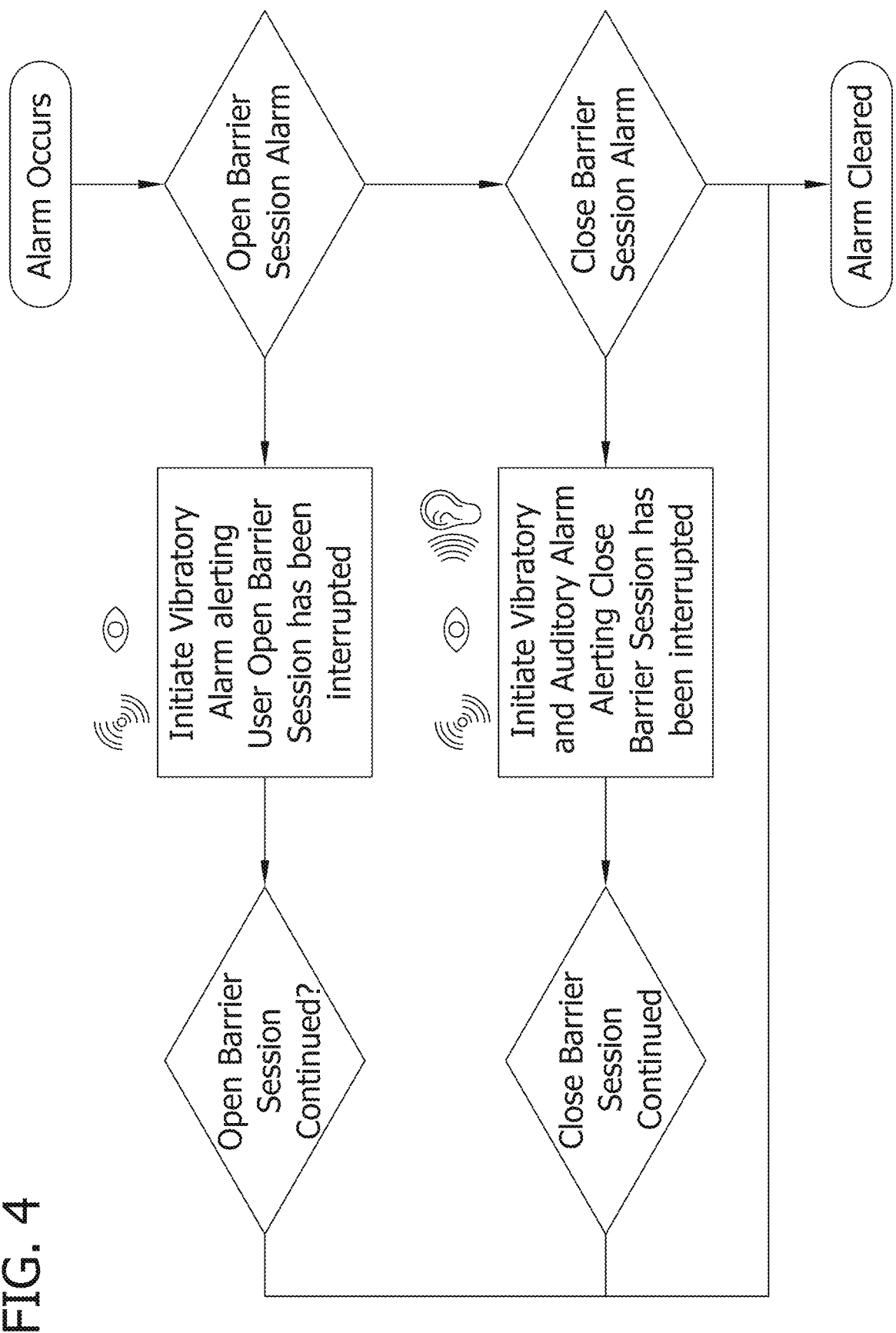
FIG. 4 is a schematic representation of a method of opening and closing the tissue barrier.
Figure 5:
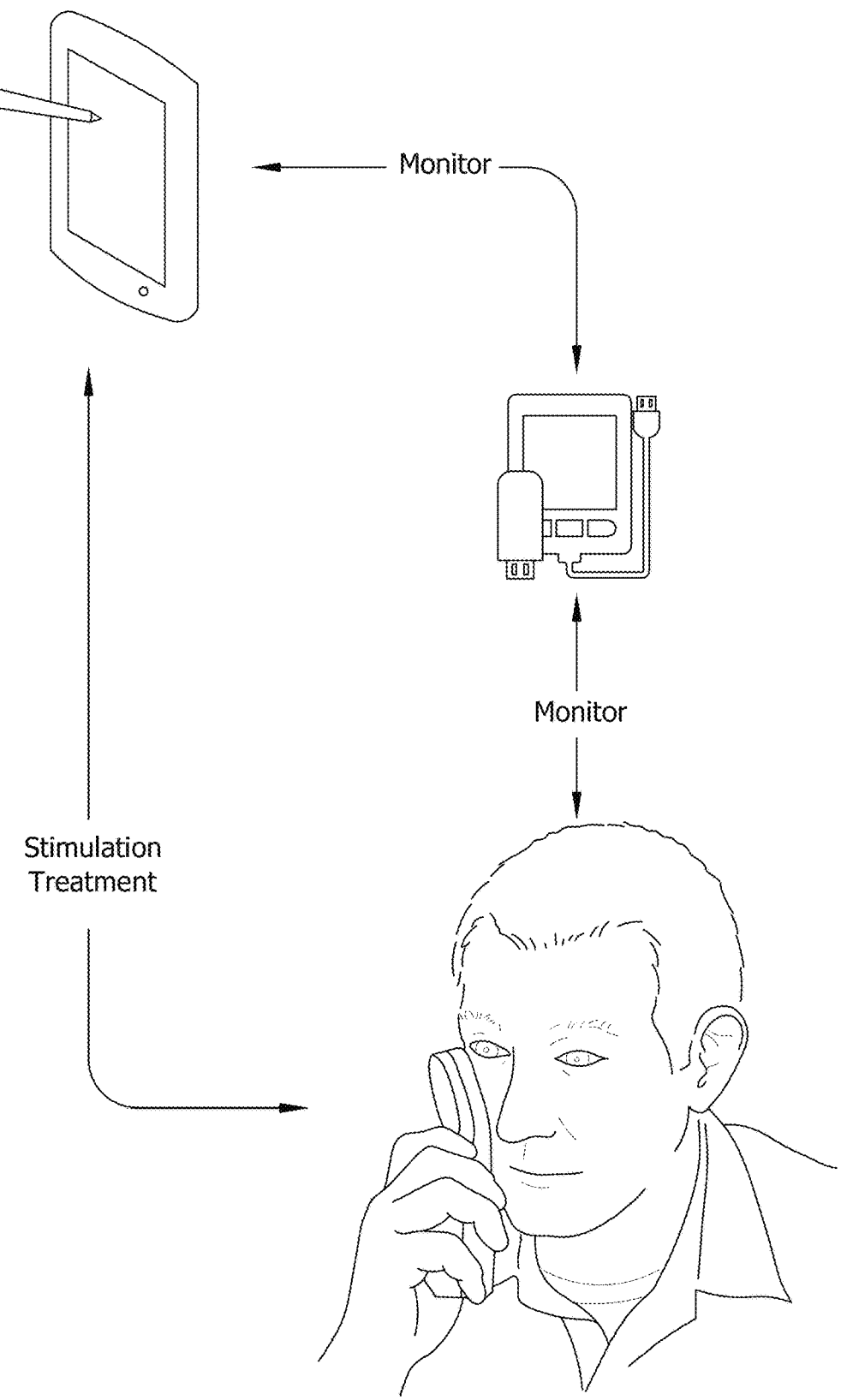
FIG. 5 is an embodiment of a system for opening and closing the BBB by stimulating the SPG.
Figure 6:
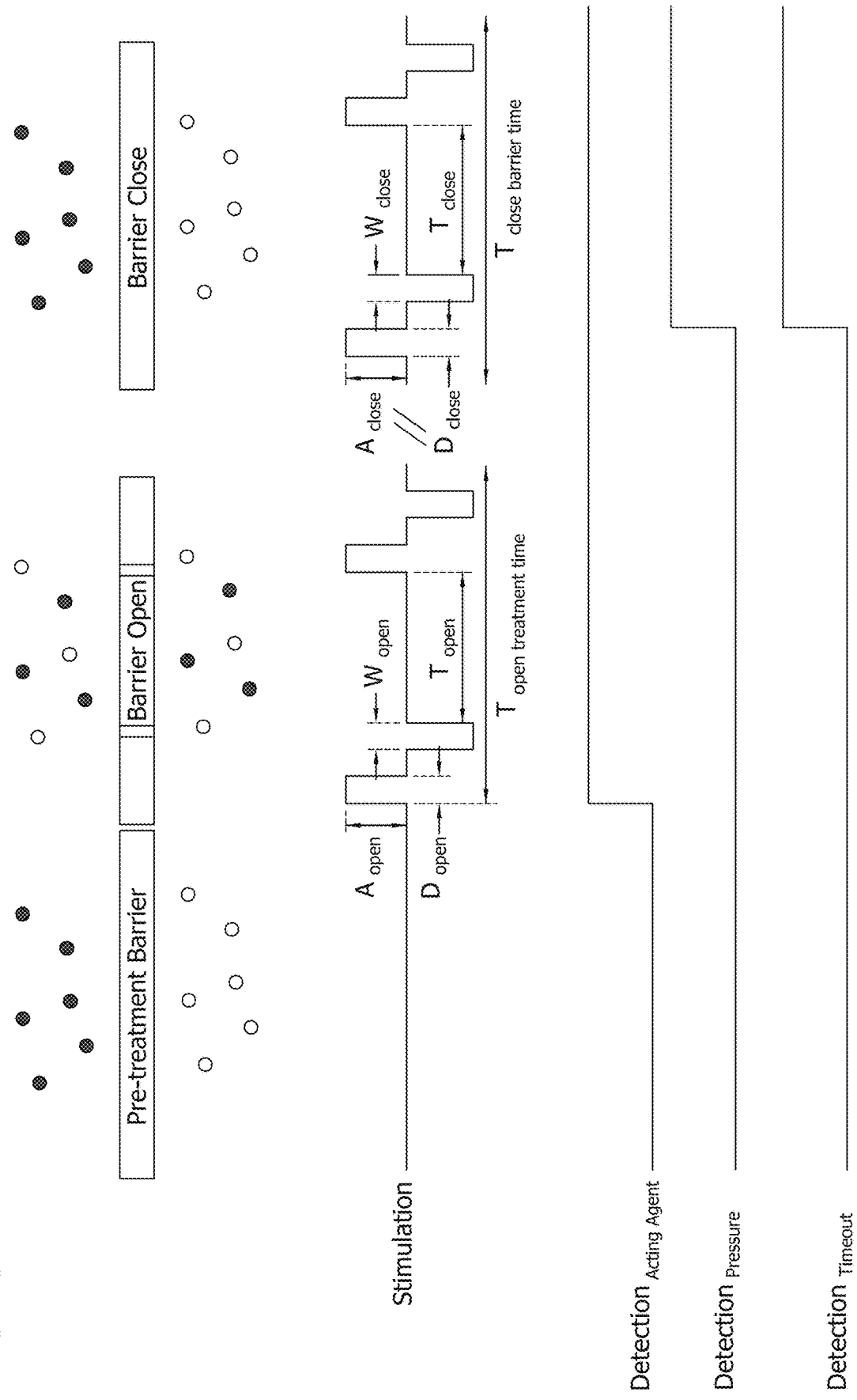
FIG. 6 is a schematic timeline of the method of treating tissue by opening and closing a tissue barrier.

Referring to FIG. 4, upon determining the detected parameter indicates the active agent is available for passing through the barrier (e.g., meets the predetermined parameter threshold), the system is operated to selectively open the barrier. The system may automatically initiate the stimulation or may indicate to the user that stimulation can begin and the user manually initiates the stimulation. The system may include any of the stimulators set forth above, including implanted electrode for stimulating ganglia (e.g., SPG). In one particular example shown in FIGS. 1 and 5, an electrode may be implanted in the subject and powered by an external power unit. As a non-limiting example, electrical stimulation applied to the SPG to open the BBB may have a frequency of 10-60 Hz (e.g., about 10-Hz), current of 0.1 to 3 mA, and a bi-phasic waveform. (Further discussion of examples of the applied stimulation is described below.) The stimulation continues until a predetermined parameter is reached indicating that a suitable amount of active agent has passed through the barrier. This parameter may be, for example, elapsed time, active agent concentration in tissue or space interior of barrier, or other parameters. If the continued stimulation is interrupted (e.g., connection between a hand-held device at the stimulator is lost), the system may be programmed to initiate an alarm (e.g., auditory, visual, tactile alarm), which indicates to the user that stimulation was not completed. The user may then reinitiate stimulation to continue treatment.

Referring still to FIG. 4, upon determining suitable delivery of the active agent through the barrier has occurred based on the measured parameter, the system is operated to stimulate the barrier to selectively close the barrier. The system may automatically initiate the stimulation or may indicated to the user that stimulation can begin and the user manually initiates the stimulation. The same device may be used to apply stimulation for closing the barrier, whereby the signal (e.g., electrical signal) is adjusted to a closing signal. As a non-limiting example, electrical stimulation applied to the SPG to close the BBB may have a frequency of 60-200 Hz (e.g., about 100 Hz), current of 0.1 to 3 mA, and a bi-phasic waveform. s (Further discussion of examples of the applied stimulation is described below.) In another embodiment, the stimulation for closing the barrier may be a different type of stimulation as compared to the stimulation for opening the barrier. The stimulation continues until a predetermined parameter is reached indicating the barrier is suitably closed. This parameter may be, for example, elapsed time, change in active agent concentration in tissue or space interior of barrier, or other parameters. If the continued stimulation is interrupted, the system may be programmed to initiate an alarm (e.g., auditory, visual, tactile alarm), which indicates to the user that stimulation was not completed. The user may then reinitiate stimulation to continue treatment.

Upon determining the barrier is suitably closed, the treatment is complete and the stimulation is ceased. One, more, or all of the steps performed by the system may be initiated and performed using a processor and computer-executed instructions saved in memory, each of which is part of the system. In this way, the treatment may be performed autonomously with no or minimal user input.

As set forth above, this exemplary method may be used to treat and deliver active agents to the brain (i.e., affect porosity of the BBB), joints (i.e., affect porosity of synovial membrane), bursa sacs (i.e., affect porosity of bursae wall). Other treatments involving other types of barriers are contemplated.

Figure 10:
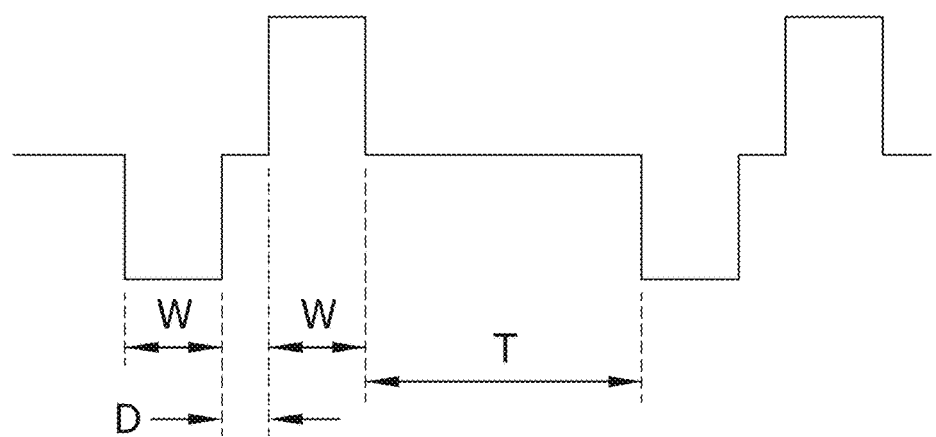
FIG. 10 is a biphasic waveform.
Figure 14:
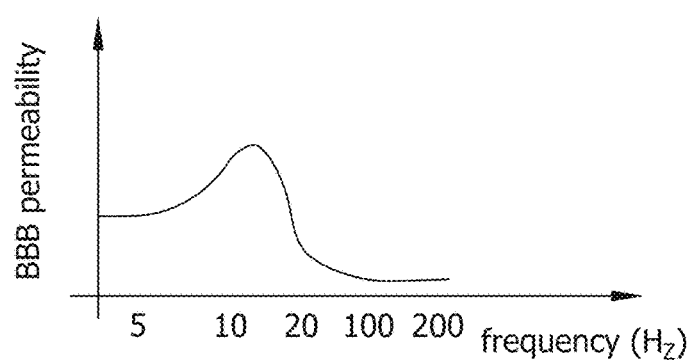
FIG. 14 is an illustrative graph showing BBB permeability as a function of frequency of the electrical stimulation.

Referring to FIG. 14, the permeability of the BBB modulated by SPG electrical stimulation is frequency dependent. As shown generally in FIG. 14, when the frequency is low (e.g., approximately 5 Hz), the BBB permeability is similar to no SPG stimulation (baseline permeability). When the frequency is increased to about 10 Hz, the permeability of the BBB is greater than baseline permeability. When the frequency is increased to about 100 Hz or greater, the permeability of the BBB decreases and is less than baseline permeability. In one example, the electrical waveform stimulation to the SPG is a biphasic, charge-balanced waveform where the pulse width is matched to maintain a charge-balanced system. A suitable waveform is shown in FIG. 10. Other suitable waveforms may be used.

Figure 11:
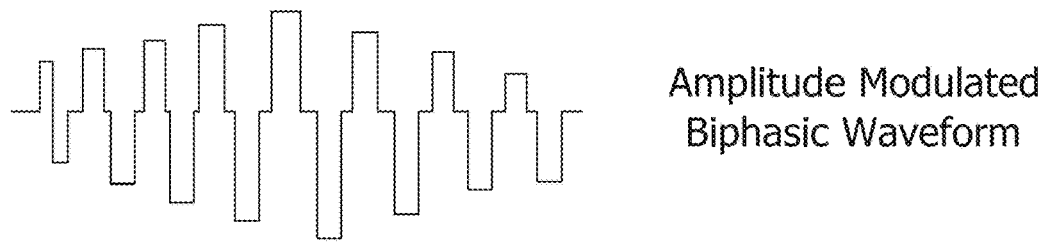
FIG. 11 is an amplitude bi-phasic waveform amplitude modulated with a sinusoidal frequency.
Figure 12:
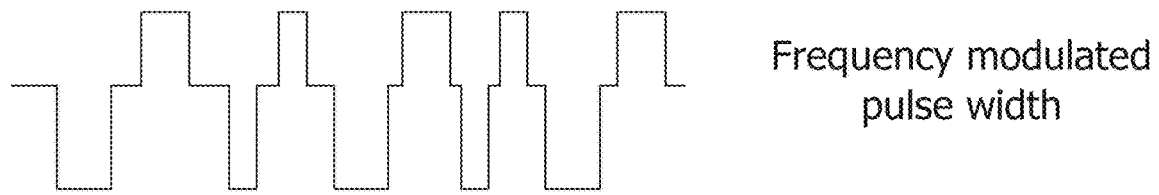
FIG. 12 is a frequency modulation waveform created by modulating the pulse width.
Figure 13:
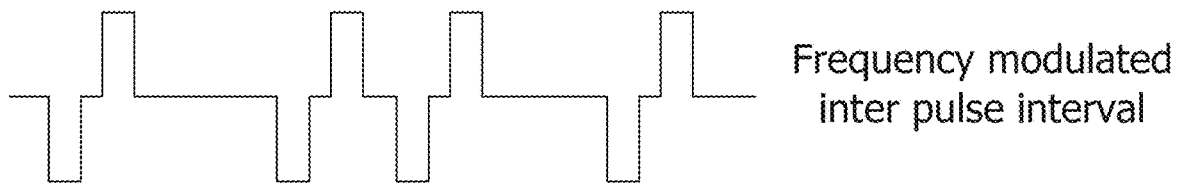
FIG. 13 is a frequency modulation waveform created by modulating the inter pulse frequency.

The waveform can be amplitude or frequency modulated. In one example, the amplitude bi-phasic waveform is amplitude modulated with a sinusoidal frequency, such as shown in FIG. 11. In other examples, amplitude modulated with charge-balanced biphasic waveform may be ramp, sawtooth, or triangle. As examples, frequency modulation waveforms can be created by either modulating the pulse width, such as shown in FIG. 12, or the inter pulse frequency, such as shown in FIG. 13. In another example, the configuration of the electrodes of the device can be modulated to change the treatment field. In particular, the anode and cathode configuration can be reversed to create changes in the magnetic field. This may be used in combination with amplitude/frequency modulation or independently. Additionally, it is considered that monopolar waveforms which are not charged balanced can be used.

Research has suggested that one mechanism of BBB opening and closing (i.e., increasing and decreasing porosity/permeability) is regulated by nitric oxide and/or other nitrogen-based molecules or compounds. In particular, it is believed that suitable stimulation of the SPG (such as at 10 Hz) releases nitric oxide (NO) from vascular endothelia. Nitric oxide (NO) is a key signaling molecule involved in vasodilation. When released, NO relaxes the smooth muscle cells in the walls of blood vessels, causing them to dilate (such as 40% or more dilated), thereby increasing permeability of BBB. In addition, nitric oxide causes proteins at the BBB to shorten or coil up, leading to increase permeability at the BBB. For example, it is believed that nitric oxide causes tight junction (TJ) proteins (e.g., actin, claudin, occluin) to shorten to increase permeability of the BBB at the TJ proteins. Further, it is believed that stimulation affects the transendothelial electrical resistance contributed by claudin and occluding proteins (e.g., zonula occludens). That is, transendothelial electrical resistance is reduced at lower frequencies, such as 10 Hz. Stimuli at 20 hertz and above (up to 100 hz or greater) cause SPG to mediate reduction in porosity or closing of BBB. This higher frequency (and other waveforms) create nitric oxide mediated response (stops release of nitric oxide) to affect endothelial proteins to uncoil and close BBB and induces vasoconstriction. This coil/uncoil protein response is reversible via electrical stimuli at SPG or other autonomic nerve fibers. At this higher frequency, the transendothelial electrical resistance is also increased.

This response can also occur outside the CNS and affect vasculature and permeability of molecules including antibodies and stem cells to the rest of the human body (including pharmaceuticals and chemotherapy agents, hormones, nutrients) to specific peripheral locations in the body to target specific tissue locations for therapy. Thus, electrical stimulation can be used on other parts of the nervous system at locations other than SPG. Stimulation of autonomic system can control throughout body similar responses-sympathetic nerves can close membranes by contraction of vasculature—parasympathetic cause expansion/dilation of vessels and or opening of vascular membranes—proteins responses similar to above.

In one or more embodiments, stimulation-induced regulation of the BBB, such as described above, may be combined with modification of the active agent to target transporters of the BBB and/or enhance penetration into brain tissue once across the BBB. Transporter proteins are present on the surface of endothelial cells lining the blood vessels in the brain. These transporters play a crucial role in regulating the entry and exit of various substances into and out of the brain through the junction (e.g., tight junctions) of the BBB. Some substances, including essential nutrients, glucose, and certain ions, are transported actively across the BBB by specific transporter proteins. Researchers design drugs or modify existing drugs to interact with these specific transporters. This involves incorporating chemical structures or functional groups that can be recognized by the transporters responsible for shuttling essential substances across the BBB. The goal is to create drug molecules that are carried on these transporters, facilitating their transport across the BBB. These transporters can be exploited for drug delivery by designing drug molecules that mimic the structure of substances that are actively transported into the brain. Amino acid transporters are another target. Certain drugs can be designed to resemble amino acids, taking advantage of the transport systems that actively move amino acids across the BBB. Some drugs can be designed to bind to specific receptors on the surface of BBB endothelial cells. This binding can trigger receptor-mediated endocytosis, allowing the drug to be transported into the brain. Nanoparticles and carrier systems can be engineered to encapsulate drugs and exploit specific transporters for BBB penetration. These carriers may include liposomes, micelles, or other nanoscale delivery vehicles. Examples of carriers are lipids (lipophylicity), transferrin receptor/ligands, hyaluronic acid, insulin receptors, lipoproteins, membrane coatings, liposomes, polymers (e.g., PGA, PLA), nanogels, gold, iron, or graphene. The attachment of a carrier to the active agent may facilitate receptor mediated transcytosis, carrier mediated transport, or transporter mediated nanocarrier.

Figure 7:
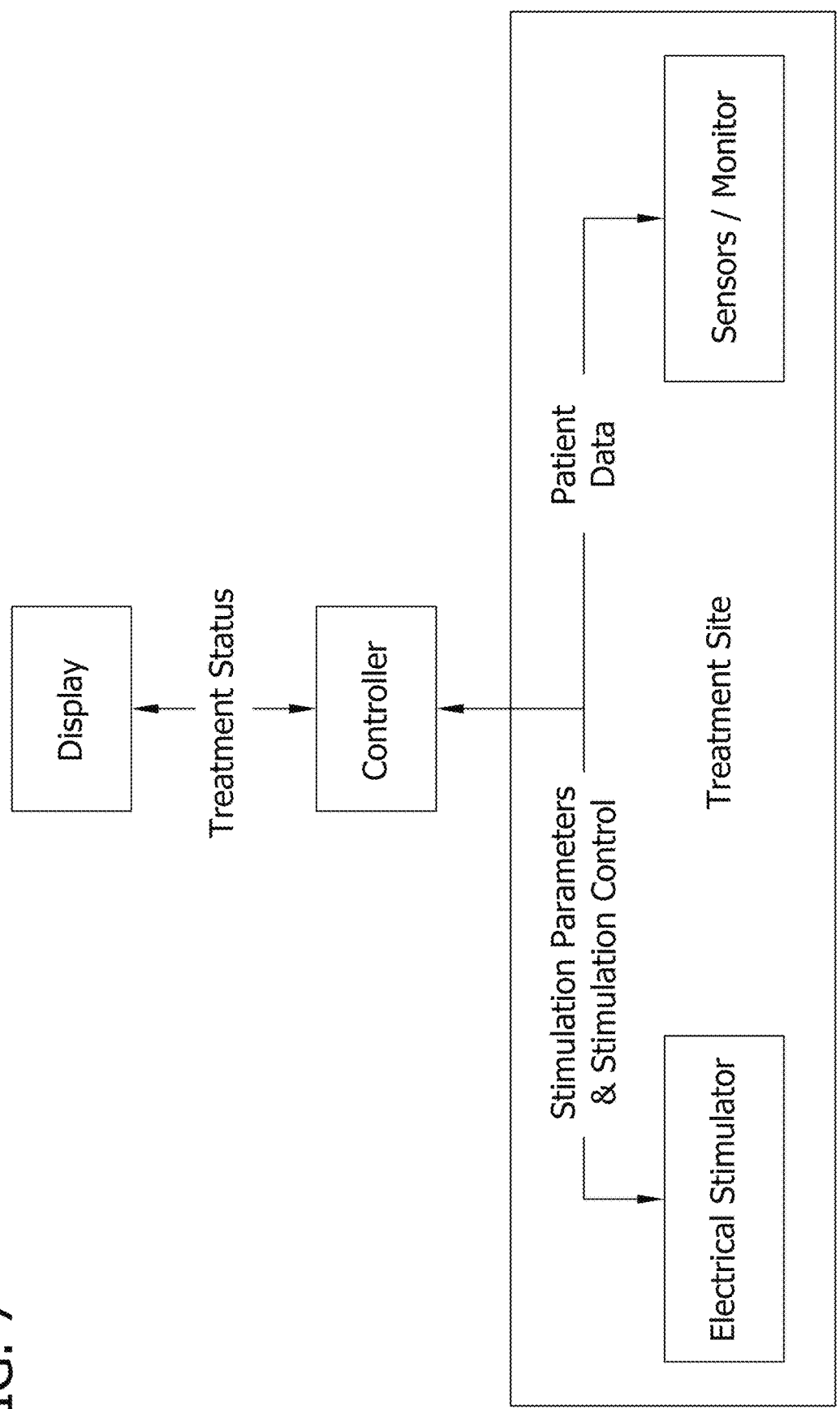
FIG. 7 is a schematic representation of one embodiment of the system for treating tissue by opening and closing a tissue barrier.
Figure 8:
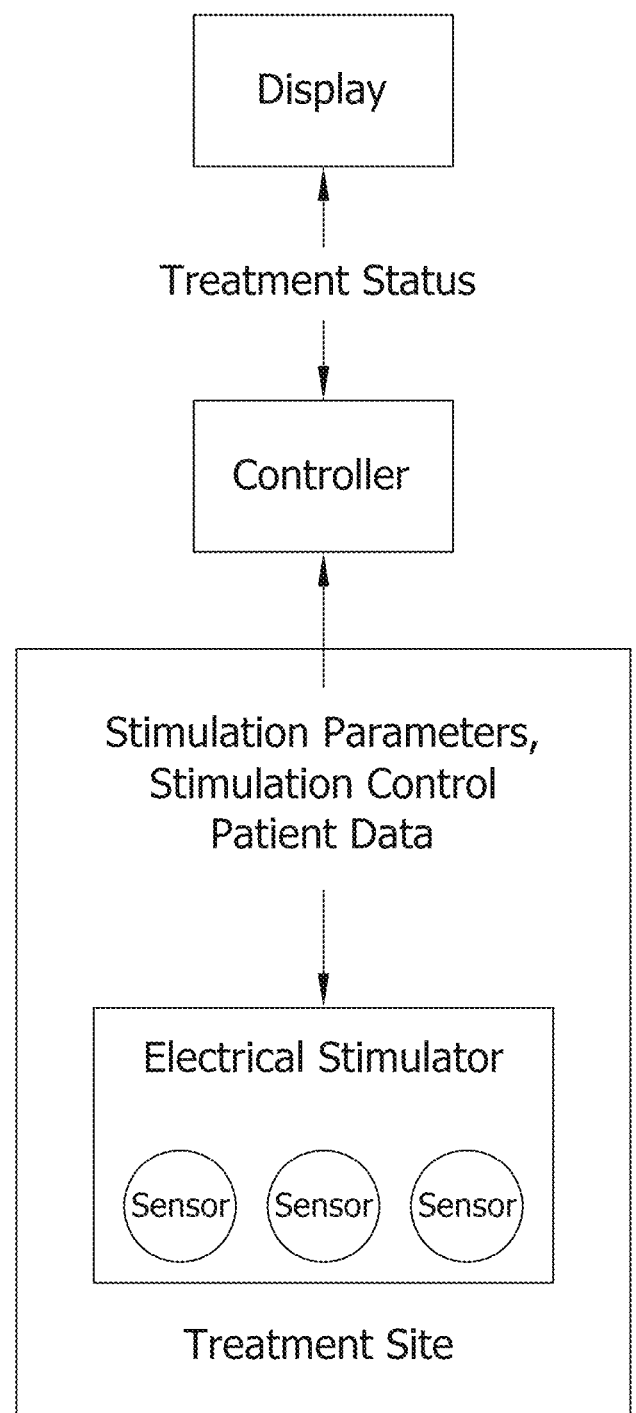
FIG. 8 is a schematic representation of another embodiment of the system.
Figure 9:
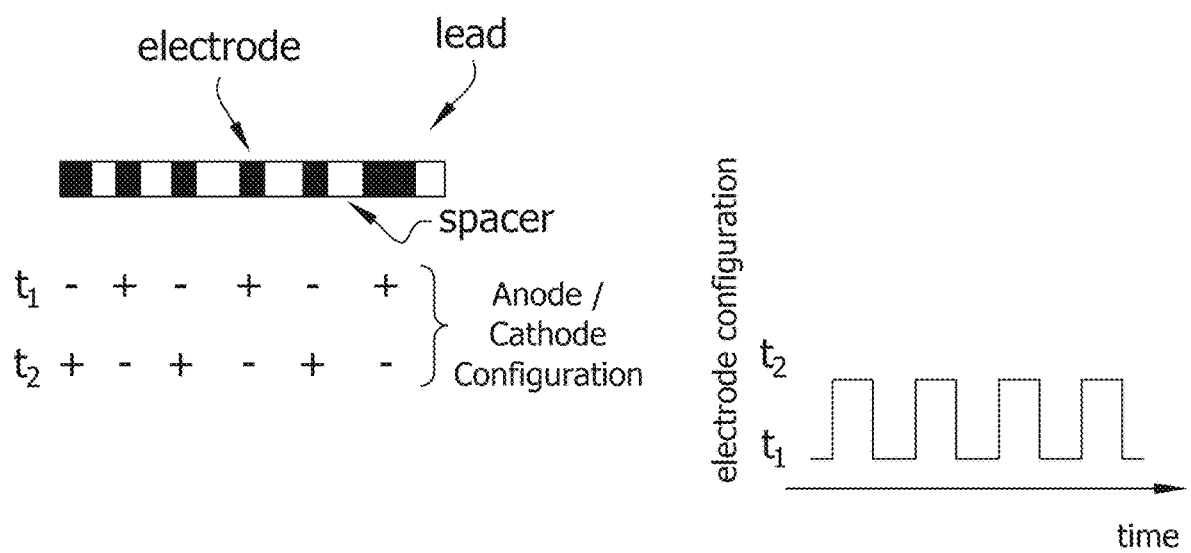
FIG. 9 is an exemplary electrode including an electrode configuration.

Referring to FIG. 7, a schematic of a suitable system for performing the described method is shown. In this embodiment, the system includes a display, a controller having a processor and memory with computer-readable instructions, a stimulator (e.g., an electrical stimulator), and sensor(s) for monitoring parameters of the patient to determine when stimuli from the stimulator should be operated. In this embodiment, the sensor(s) are separate from the electrical stimulator. In this embodiment, each of the stimulator and sensor(s) are implantable or deliverable to or adjacent the barrier. Referring to FIG. 8, a schematic of a similar system is shown. The difference being the sensor(s) are incorporated with the stimulator.

In one or more embodiments, a system and method described herein is used as treatment when the BBB has been disrupted due to ischemic or hemorrhagic strokes, or other conditions. In such a method, the disrupted BBB is brought back to normal function by controlling the opening and closing of the BBB, depending on how the function of the BBB was affected by the stroke. Proper diagnosis of the irregular function of the BBB will determine the treatment using the system and method of the present disclosure.

It is believed that one potential adverse effect of opening the BBB is edema in or around the brain. This can result from oncotic forces generated by influx of fluids and particles into the brain. In one embodiment, the intracranial pressure and brain edema of the patient could be monitored while the BBB is disrupted. This could be done by with MRI, a pressure sensor, transcranial ultrasound with Doppler, blood pressure, or any combination of these methods. Other methods known in the art can be used as a stand monitor or combined. In one example, correlation between intracranial pressure and blood pressure (absolute or relative) may be used to determine intracranial pressure. Whenever the brain edema is detected, and alert could be shown to the operator, who can adjust the treatment protocol. In another embodiment, the monitoring could be integrated into the device or two-way communication could be established between the stimulator and the monitoring equipment. Thus, these sensors can be integrated into the device similar to the integration of the active agent sensors shown in FIG. 8. When any swelling of the brain is detected, the system can adjust the stimulation produced by the stimulator (i.e., automatically change from an open signal to a closed signal) to close the BBB. By using artificial intelligence or machine learning, a predictive algorithm could be developed that would recognize the potential for swelling prior to the event and the signal could be adjusted. The biological response time to the changing signals could be calculated to optimize the opening and closing of the BBB. Additionally, it is considered that external inputs could be used to power machine learning methods such a convolutional neural network including but not limited to MRI, EEG, MEG. Additionally, drug uptake could be monitored, nitric oxide levels, or the transepithelial/endothelial electrical resistance (TEER) could be used.

It is also believed that using frequency that is optimal for opening the BBB may increase potential for edema or the size of particle targeted for delivery across the BBB. To optimize the therapy and maintain patient safety, a lower frequency such as 5 Hz could be selected to partially open the BBB. In another example, modulation techniques are used to create a signal for creating variable permeability of the BBB. In one embodiment the neuromodulation signal applied to the SPG could frequency shift between the "open" and "close" signals. It is also considered that pulse width modulation, frequency modulation, amplitude modulation, or other known techniques could be used to optimize the signal for the desired porosity while minimizing adverse effects.

Rather than stimulating neuron cells (e.g., SPG) to affect porosity of barrier (e.g., BBB), the system may locally stimulate the barrier (e.g., BBB, or other blood vessels at or near the brain) to open and close the barrier. Moreover, arteries may be stimulated to affect inflow or veins/lymphatics may be stimulated to affect outflow.

In one example, a catheter is delivered or "floated" to specific location in the brain to stimulate local blood vessel/autonomic system to open or close electrically. This could be controlled to time opening or dilation with delivery of a medication, therapy, or cellular treatment by longing drug release to opening then closing to limit risk of intracranial swelling or complications due to pressure or osmotic differentials. This is considered local and direct stimulation of the barrier (e.g., SPG) rather than stimulating neurons (e.g., ganglia) to affect the barrier. Frequency and/or amplitude of the electrical signal may be adjustable to adjust porosity of the blood vessel and/or dilation of the blood vessel. Stimulation may also be imparted on a cellular basis to enhance medication or therapeutic treatment across a cell membrane or a micro level.

In one or more embodiments, a coating of the implantable electrode could be partially biodegradable to act as an insulator then when it degrades even partially electrode or electronic device loses functional ability. The electrode could also be partially ingrowth capable to so a cuff or section with tissue ingrowth capability which stabilized electrode or delivery through motion or activity. The porosity of ingrowth would optimally be less than 400 microns and could be temporary stabilized by suture anchors, e.g., knotless anchors for MIS applications to stabilize to fascia or tissue or bone. It is also considered that may be indication where ingrowth or a permanent implant is not required. In this situation it may be preferred to insert a temporary electrode which could be inserted in a similar method to a SPG block, although other methods could be used. Non-electrical stimulation could be used as well, which could include direct manipulation of the SPG, or external stimulation with transcranial magnet stimulation, high intensity focused ultrasound (HiFu), or low intensity pulsed ultrasound (LIPUS).

When opening the BBB via SPG stimulation, LIPUS, HiFu or other methods it will be critical to protect the CNS from unintended exposure to medicines that might already be in the patients' bloodstream during therapy. In one embodiment of this invention, this can be done through software by creating a database of all prescription and over the counter medicines and supplements that a patient is currently taking and the dosing schedule. By using the known absorption rates of these drugs, half-life, and size of the drug molecule a treatment schedule can be created for each patient, which could show the optimal time to perform a therapy to relax the BBB. It is also considered that this therapy schedule could be block therapy from being delivered to a patient during times that levels of pharmaceutical are present that could be dangerous to the CNS.

The system can also be configured to integrate into a hospital network to pull the patient information and medication lists through defined protocols such as Health Level 7 (HL7). Information could also be imported from cell phone applications. This software can also be used to calculate the optimal time to deliver a drug to a patient intended to cross the BBB, as well as the optimal time to perform therapy.

Figure 15:
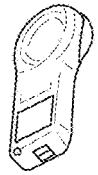
FIG. 15 is a standalone, handheld device for operating the stimulator.

In one or more embodiments, a medical device, such as the neurostimulator or other medical device used by a patient, has capability for billing by use of the device. To allow for billing the therapy, multiple hardware and software solution can be implemented depending on design constraints. In FIG. 15 a stand along configuration is shown. This configuration is the simplest and does not require an internet connection to the handheld or programming tablet. If this configuration, a total amount of uses, a valid date range, or a combination of the two could be loaded on the device. When the user has excited the amount of total uses, or the valid usage dates have expired, the user could be required to bring the device back to the healthcare professionals office where additional time can be added and required maintenance performed (if required) on the handheld.

Figure 16:
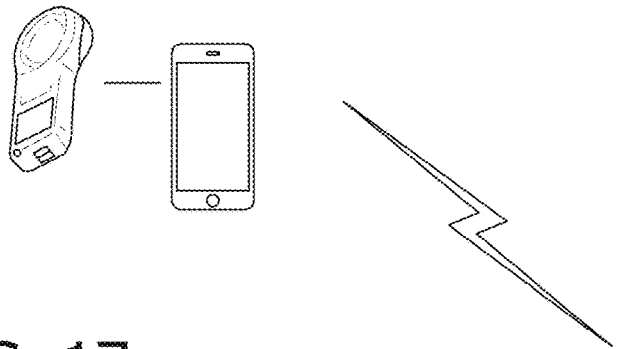
FIG. 16 is the handheld device tethered to and in electrical communication with a smart mobile device.
Figure 17:
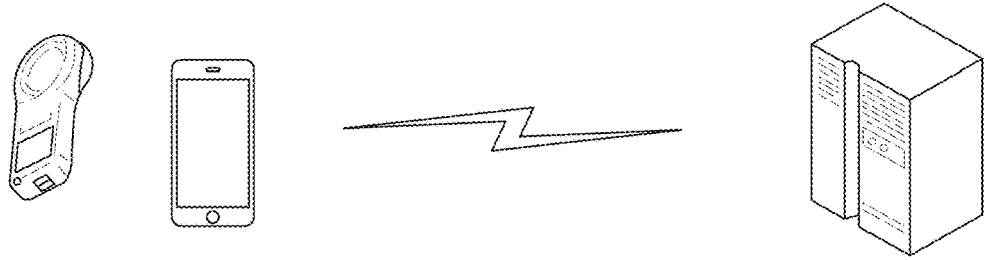
FIG. 17 is the handheld device in wireless communication with a smart mobile device.
Figure 18:
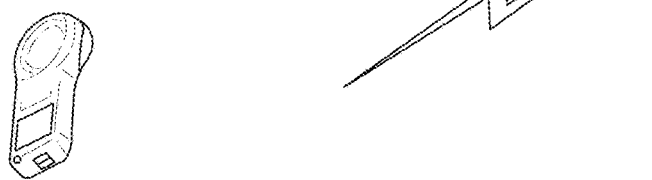
FIG. 18 is the handheld device in direct communication with a remote server.

Alternatively, it is considered that the handheld device can be connected to the internet via a tethered connection (FIG. 16). This could be a smart phone, a dedicated device, a laptop, tablet or personal computer. An application running on the tethered device would communicate with remote servers, which could update the total number of uses and upload usage information for review by the company or healthcare professionals. In FIG. 17, a configuration is shown which the cable tether between the phone, tablet, or computer could be removed by using a known wireless protocol such as BlueTooth or WiFi.

Alternatively, a system could be made there the remote connected directly to the internet. This could be done via WiFi, cellular connection, or other known connection methods. In this configuration, the handheld device would communicate directly with the company servers. Allowing the ability for real time usage, billing, and usage information to be reported to the company.

Modifications and variations of the disclosed embodiments are possible without departing from the scope of the invention defined in the appended claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A method of modulating a blood-brain barrier (BBB) of a subject comprising:
    applying a first electrical stimulation to the subject to stimulate a sphenopalatine ganglion (SPG) of the subject, wherein said applying the first electrical stimulation actively increases porosity of the BBB from an initial porosity to an increased porosity; and
    applying, after said applying a first electrical stimulation, a second electrical stimulation to the subject to stimulate the SPG of the subject, wherein said applying the second electrical stimulation actively decreases porosity of the BBB from the increased porosity to a decreased porosity that is less than the increased porosity.

2. The method of modulating a BBB of a subject set forth in claim 1, wherein a frequency of the first electrical stimulation is less than a frequency of the second electrical stimulation.

3. The method of modulating a BBB of a subject set forth in claim 2, wherein frequency of the first electrical stimulation is from about 10 Hz to about 60 Hz.

4. The method of modulating a BBB of a subject set forth in claim 3, wherein the frequency of the second electrical stimulation is from about 60 Hz to about 200 Hz.

5. The method of modulating a BBB of a subject set forth in claim 1, further comprising delivering an agent into bloodstream of the subject, whereby the agent passes through the BBB due to the increased porosity of the BBB.

6. The method of modulating a BBB of a subject set forth in claim 1, wherein the first and second electrical stimulations are bi-phasic waveforms.

7. The method of modulating a BBB of a subject set forth in claim 1, further comprising:

monitoring, after said applying a first electrical stimulation, a parameter of the BBB; and determining, based on the monitored parameter and before said applying a second electrical stimulation, when porosity of the BBB has increased from the initial porosity to the increased porosity based on the monitored parameter.

8. The method of modulating a BBB of a subject set forth in claim 7, wherein the parameter of the BBB is at least one of: agent concentration at the BBB, change in agent concentration in a brain of the subject, and change in concentration of a substance from the brain in blood of the subject.

9. The method of modulating a BBB of a subject set forth in claim 7, wherein said monitoring comprises sensing, using a sensor, the parameter.

10. The method of modulating a BBB of a subject set forth in claim 9, wherein said determining comprises: receiving using a control unit a signal from the sensor indicative of the sensed parameter; and determining, using the received signal, when porosity of the BBB has increased from the initial porosity to the increased porosity.

11. The method of modulating a BBB of a subject set forth in claim 7, wherein each of said applying a first electrical stimulation and said applying a second electrical stimulation is performed using at least one electrode implanted in the subject.

* * * * *

UNITED STATES PATENT AND TRADEMARK OFFICE
CERTIFICATE OF CORRECTION

| | | |
|---|---|---|
| PATENT NO. | : 12,383,735 B2 | Page 1 of 1 |
| APPLICATION NO. | : 18/649710 | |
| DATED | : August 12, 2025 | |
| INVENTOR(S) | : Bonutti et al. | |

It is certified that error appears in the above-identified patent and that said Letters Patent is hereby corrected as shown below:

On the Title Page

Item (73) Assignee, Please change "P Tech, LLC" to --Realeve, LLC Manalapan FL (US)--.

Signed and Sealed this
Sixteenth Day of September, 2025

Coke Morgan Stewart
*Acting Director of the United States Patent and Trademark Office*